United States Patent [19]

Yellin et al.

[11] Patent Number: 4,746,672
[45] Date of Patent: May 24, 1988

[54] OXIDES OF 1,2,5-THIADIAZOLES, THEIR USE IN PHARMACEUTICAL COMPOSITIONS

[75] Inventors: Tobias O. Yellin, Fremont, Calif.; Philip N. Edwards, Bramhall; Michael S. Large, Congleton, both of England

[73] Assignee: ICI Americas Inc., Wilmington, Del.

[21] Appl. No.: 376,395

[22] Filed: May 10, 1982

[51] Int. Cl.$^4$ ............................ A61K 31/41; C07D 417/12
[52] U.S. Cl. .................................... 514/362; 544/134; 544/357; 544/367; 546/187; 546/209; 546/256; 546/277; 548/128; 548/129; 548/130; 548/135
[58] Field of Search ............... 548/135, 134, 128, 129, 548/130; 424/269; 514/362

[56] References Cited

U.S. PATENT DOCUMENTS

| | | | |
|---|---|---|---|
| 4,165,377 | 8/1979 | Jones et al. | 548/337 |
| 4,165,378 | 8/1979 | Gilman et al. | 548/337 |
| 4,234,735 | 11/1980 | Jones et al. | 548/198 |
| 4,242,350 | 12/1980 | Yellin et al. | 548/130 |
| 4,242,351 | 12/1980 | Yellin et al. | 548/133 |
| 4,262,126 | 4/1981 | Gilman et al. | 548/193 |
| 4,309,435 | 1/1982 | Yellin et al. | 548/134 |
| 4,315,009 | 2/1982 | Jones et al. | 548/193 |
| 4,332,949 | 6/1982 | Yellin et al. | 548/128 |
| 4,338,447 | 7/1982 | Yellin et al. | 548/133 |
| 4,338,448 | 7/1982 | Yellin et al. | 548/133 |
| 4,342,765 | 8/1982 | Jones et al. | 548/128 |
| 4,347,370 | 8/1982 | Gilman et al. | 548/193 |
| 4,362,728 | 12/1982 | Yellin et al. | 544/360 |
| 4,374,836 | 2/1983 | Yellin et al. | 544/182 |

FOREIGN PATENT DOCUMENTS

| | | |
|---|---|---|
| 866155 | 4/1977 | Belgium . |
| 0040696 | 12/1981 | European Pat. Off. ............ 548/135 |
| 2067987 | 8/1981 | United Kingdom . |

*Primary Examiner*—Glennon H. Hollrah
*Assistant Examiner*—James H. Turnipseed

[57] ABSTRACT

Sulphur derivatives which are histamine H-2 antagonists and which inhibit gastric acid secretion of the formula I:

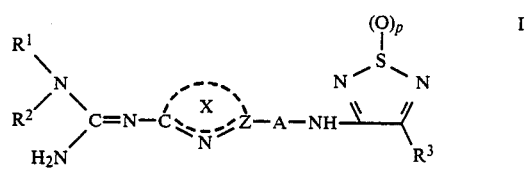

in which $R^1$ and $R^2$ independently are hydrogen or 1–10C alkyl, 3–8C cycloalkyl or 4–14C cycloalkylalkyl, each alkyl, cycloalkyl or cycloalkylalkyl optionally carrying one or more F, Cl or Br atoms, provided that one of $R^1$ and $R^2$ is halogen substituted; ring X is a heterocyclic ring as defined in the specification; A is phenylene or 5–7C cycloalkylene or a 1–8C alkylene chain into which is optionally inserted one or two groups; p is 1 or 2; $R^3$ is a variety of radicals described in the specification; and the pharmaceutically-acceptable acid-addition salts thereof. Manufacturing processes for the derivatives, intermediates and pharmaceutical compositions are also part of the invention.

10 Claims, No Drawings

OXIDES OF 1,2,5-THIADIAZOLES, THEIR USE IN PHARMACEUTICAL COMPOSITIONS

This invention relates to sulphur derivatives which are histamine H-2 antagonists and which inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, *Brit. J. Pharmac.* 1966, 27, 427) and the action of histamine at this receptor is blocked (antagonized) by classical "antihistamine" drugs such as mepyramine. The second histamine receptor has been named the H-2 receptor (Black et al., *Nature*, 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In UK published Patent Application No. 2067987 are described histamine H-2 receptor antagonists which are guanidino heterocycles carrying a side chain to the end of which is attached an oxidized thiadiazole ring. It has now been discovered that if the guanidine radical is substituted by a haloalkyl radical there are produced compounds which are potent histamine H-2 receptor antagonists.

According to the invention there is provided a guanidine derivative of the formula I:

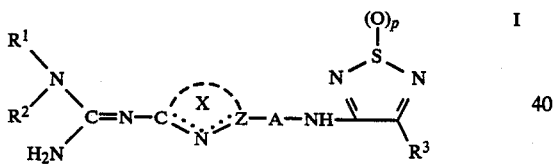

in which $R^1$ and $R^2$, which may be the same or different, are hydrogen atoms or branched or unbranched 1–10C alkyl, 3–8C cycloalkyl or 4–14C cycloalkylalkyl radicals, each alkyl, cycloalkyl or cycloalkylalkyl radical being optionally substituted by one or more halogen atoms selected from fluorine, chlorine and bromine atoms, provided that at least one of $R^1$ and $R^2$ is a halogen-substituted alkyl, halogen-substituted cycloalkyl or halogen-substituted cycloalkylalkyl radical, and provided that there is no halogen substituent on the carbon atom of the alkyl, cycloalkyl or cycloalkylalkyl radical which is directly attached to the nitrogen atom; in ring X the dotted line is a double bond on one side of the nitrogen atom N and Z is a carbon or nitrogen atom such that ring X is a 5- or 6-membered aromatic heterocyclic ring which contains at least one nitrogen atom and may optionally contain one or two additional hetero atoms selected from oxygen, nitrogen and sulphur atoms, which heterocyclic ring may, where possible, carry one or two optional substituents, the optional substituents on ring X being selected from fluorine, chlorine and bromine atoms and 1–6C alkyl, 1–6C alkoxy, 1–6C alkylthio, trifluoromethyl, hydroxy and amino radicals;

A is a 1–8C alkylene chain which is optionally substituted by one or two 1–3C alkyl radicals and into which is optionally inserted, as part of the backbone of the chain, one or two groups selected from oxygen and sulphur atoms, NH, 1–6C N-alkyl radical and cis and trans vinylene, ethynylene, phenylene and 5–7C cycloalkylene radical provided that no two insertions selected from oxygen and sulphur atoms and NH and N-alkyl radicals are directly attached one to the other and provided that when an insertion is directly attached to the NH radical it is other than an oxygen or sulphur atom or an NH or N-alkyl radical, or A is a 5–7C cycloalkylene or phenylene radical;

p is 1 or 2;

$R^3$ is a hydroxy radical or a radical of the formula $NR^4R^5$ in which $R^4$ and $R^5$, which may be the same or different, are hydrogen atoms or radicals selected from 1–6C alkyl, 3–6C alkenyl, 3–6C alkynyl, 3–6C cycloalkyl, 4–10C cycloalkylalkyl, 2–6C hydroxyalkyl, 3–8C alkoxyalkyl, 3–8C alkylthioalkyl, 2–6C aminoalkyl, 3–8C alkylaminoalkyl, 4–12C dialkylaminoalkyl, 6–13C pyrrolidinoalkyl, 7–14C piperidinoalkyl, 6–13C morpholinoalkyl, 6–13C piperazinoalkyl, 6–12C pyridylalkyl, amino, 1–6C alkylamino, 2–10C dialkylamino, 2,2,2-trifluoroethyl, 2-fluoroethyl, hydroxy, 1–6C alkoxy, 2,3-dihydroxypropyl, cyano, 2–6C cyanoalkyl, amidino, 2–6C alkylamidino, phenyl and 7–12C phenylalkyl radicals, in the latter two of which the benzene ring is optionally substituted by 1 or 2 groups selected from halogen atoms and 1–6C alkyl, hydroxy and 1–6C alkoxy radicals or by a methylenedioxy, trifluoromethyl or 2–8C dialkylamino radical, with the proviso that $R^4$ and $R^5$ cannot both be cycloalkylalkyl, optionally-substituted phenyl, amino, alkylamino, dialkylamino, hydroxy, alkoxy, cyano, amidino or alkylamidino radicals, or $R^5$ is a hydrogen atom and $R^4$ is a radical of the formula II:

$$-(CH_2)_n-E-(CH_2)_m-Het \qquad II$$

in which m is 0, 1 or 2, n is 2, 3 or 4, E is an oxygen or sulphur atom or a methylene radical, Het is a phenyl, imidazolyl, thiazolyl, isothiazolyl, oxazolyl, isoxazolyl, triazolyl, thiadiazolyl, oxadiazolyl, furyl, thienyl or pyridyl radical, each of which is optionally substituted by 1 or 2 substituents, the first substituent being chosen from halogen atoms and 1–6C alkyl, hydroxy, trifluoromethyl, amino, hydroxymethyl and 1–6C alkoxy radicals and radicals of the formulae III, IV and V:

—(CH$_2$)$_q$NR$^9$R$^{10}$    V in which R$^1$ and R$^2$ have the meanings given independently above, q is 0, 1, 2, 3, 4, 5 or 6, R$^7$ and R$^8$, which may be the same or different, are hydrogen atoms or 1–6C alkyl, 3–6C alkenyl, 3–6C alkynyl, 1–6C alkanoyl or benzoyl radicals or R$^7$ and R$^8$ are together an ethylene radical, and R$^9$ and R$^{10}$, which may be the same or different, are hydrogen atoms or 1–6C alkyl, 3–6C alkenyl, 3–6C alkynyl, 3–6C cycloalkyl or phenyl radicals provided that R$^9$ and R$^{10}$ cannot both be cycloalkyl or phenyl radicals, or R$^9$ and R$^{10}$, together with the nitrogen atom to which they are attached, is a pyrrolidino, morpholino, piperidino, methylpiperidino, N-methylpiperazino or homopiperidino radical, and the second substituent being chosen from halogen atoms and 1–6C alkyl, hydroxy, trifluoromethyl, amino, hydroxymethyl and 1–6C alkoxy radicals, or R$^4$ and R$^5$ together represent a radical of the formula VI:

—CH$_2$CH$_2$—Y—(CH$_2$)$_r$—    VI in which r is 1, 2 or 3, Y is an oxygen or sulphur atom or a methylene radical or a radical of the formula NR$^9$; and the pharmaceutically-acceptable acid-addition salts thereof.

It is to be understood that, in the above formula I and throughout this specification, although the double bond in the guanidine residue attached to ring X has been inserted in a particular position, other tautomeric forms are possible, and this invention includes such tautomeric forms within its scope, both in terms of the compounds of the invention and in terms of the manufacturing processes. It is also to be understood that when A is or contains a cycloalkylene radical the groups attached to this radical may be in the cis or trans configuration. When A is or contains a cycloalkylene radical and/or when A is an alkylene chain substituted by one or two alkyl radicals, the compound of the formula I will, in most instances, contain at least one asymmetric centre. In such cases the compound of the formula I will therefore exist in at least two enantiomeric forms, the precise number being determined by the number of asymmetric centres. The biological activity, as hereinafter defined, of these enantiomeric forms may differ, and it is therefore to be understood that this invention encompasses the racemate of the formula I, including any possible diastereoisomeric forms, and any enantiomeric form which possesses the disclosed biological activity, it being a matter of common general knowledge to one skilled in the art how to separate diastereoisomeric forms and how to separate a racemate into its enantiomers and determine the biological activity of each.

A particular value for R$^1$ or R$^2$ when it is a halogen-substituted alkyl radical is a 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3-tetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3-pentafluoroisopropyl, 1,3-difluoroisopropyl or 2,2,3,3,4,4,4-heptafluorobutyl radical.

A particular value for R$^1$ or R$^2$ when it is a halogen-substituted cycloalkyl radical is a 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl or 2-chloro-2,3,3,4,4-pentafluorocyclobutyl radical.

A particular value for R$^1$ or R$^2$ when it is a halogen-substituted cycloalkylalkyl radical is a (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl or (2-chloro-1,2,3,3,4,4-hexafluorocyclobutyl)methyl radical.

A particular value for R$^1$ or R$^2$ when it is an alkyl radical is a methyl, ethyl, n-propyl, isopropyl or butyl radical.

A particular value for R$^1$ or R$^2$ when it is a cycloalkyl radical is a cyclopropyl or cyclobutyl radical.

A particular value for R$^1$ or R$^2$ when it is a cycloalkylalkyl radical is a cyclopropylmethyl or cyclobutylmethyl radical.

A particular value for ring X is an oxazole, thiazole, imidazole, 1,2,4-thiadiazole, 1,2,4-oxadiazole, 1,2,3-triazole, 1,2,4-triazole, pyrazole, pyrazine, pyridine, pyrimidine or 1,3,5-triazine ring.

A particular value for the optional substituent on ring X when it is an alkyl, alkoxy or alkylthio radical is a methyl, methoxy or methylthio radical.

A particular value for A is a trimethylene, tetramethylene, pentamethylene, thioethylene, thiotrimethylene, thiotetramethylene, thiopentamethylene, oxyethylene, oxytrimethylene, oxytetramethylene, methylenethiomethylene, methylenethioethylene, methylenethiopropylene, methyleneoxymethylene, methyleneoxyethylene, ethyleneoxyethylene, oxy-2-methylethylene, thiopropylenethiomethylene, oxyethyleneoxymethylene, iminoethylene, iminopropylene, vinylenepropylene, 1,3-phenylene, 1,3-cyclopentylene, methylene-1,4-phenylene, ethyleneoxymethylene-1,4-phenylene, oxy-1,3-phenylenemethylene or thiomethyleneethynylenemethylene radical. These values for A are written reading from left to right in formula I such that the first named part of the radical is attached to ring X and the last named part of the radical is attached to NH. Thus, for example, when A is a methylenethioethylene radical, the compound of the formula I contains the part structure VII:

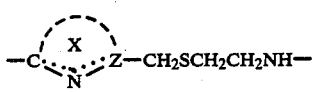

VII

A particular value for R$^4$ or R$^5$ is a hydrogen atom or a methyl, allyl, propargyl, cyclohexyl, cyclopropylmethyl, 2-hydroxyethyl, 2-methoxyethyl, 2-methylthioethyl, 2-aminoethyl, 2-methylaminoethyl, 2-dimethylaminoethyl, 2-pyrrolidinoethyl, 2-piperidinoethyl, 2-morpholinoethyl, 2-piperazinoethyl, pyrid-2-ylmethyl, amino, methylamino, dimethylamino, 2,2,2-trifluoroethyl, 2-fluoroethyl, hydroxy, 2,3-dihydroxypropyl, cyano, cyanomethyl, amidino, methylamidino, phenyl or benzyl radical, the phenyl and benzyl radicals being optionally substituted on the benzene ring by 1 or 2 groups selected from fluorine and chlorine atoms and methyl, hydroxy and methoxy radicals, or by a methylenedioxy, trifluoromethyl or dimethylamino radical.

A particular value for the first optional substituent on Het in formula II is a fluorine or chlorine atom or a methyl, hydroxy, trifluoromethyl, amino, hydroxymethyl or methoxy radical or a radical of the formula III, IV or V given above in which R$^1$ and R$^2$ have the values given above, q is 0, 1, 2, 3, 4, 5 or 6, $R^7$ and $R^8$, which may be the same or different, are hydrogen atoms or methyl, allyl, propargyl, acetyl or benzoyl radicals or $R^7$ and $R^8$ are together an ethylene radical and $R^9$ and $R^{10}$, which may be the same or different, are hydrogen atoms or methyl, allyl, propargyl, cyclohexyl or phenyl radicals, provided that $R^9$ and $R^{10}$ cannot both be cyclohexyl or phenyl radicals, or $R^9$ and $R^{10}$, together with the nitrogen atoms to which they are attached, is a pyrrolidino, morpholino, piperidino, methylpiperidino, N-methylpiperazino or homopiperidino radical.

A particular value for the second optional substituent on Het in formula II is a fluorine or chlorine atom or a methyl, hydroxy, trifluoromethyl, amino, hydroxymethyl or methoxy radical.

A further particular value for $R^4$ and $R^5$ is that they be joined to form a radical of the formula VI given above.

The following are eleven preferred features of the guanidine derivative of the formula I. When any one of these features is taken, either singly or in combination, with the other general or particular features of the guanidine derivative listed above, there are obtained preferred sub-groups of compounds within the above general definition.

1. $R^2$ is a hydrogen atom.
2. $R^1$ is a 2,2,2-trifluoroethyl, 2,2,2-trichloroethyl, 2-chloro-2,2-difluoroethyl, 2,2-difluoroethyl, 2,2,3,3-tetrafluoropropyl, 2,2,3,3,3-pentafluoropropyl, 1,1,1,3,3,3-hexafluoroisopropyl or 1,1,1-trifluoroisopropyl radical.
3. $R^1$ is a 2,2,2-trifluoroethyl radical.
4. Ring X carries no optional substituent.
5. Ring X is a pyrimidine in which A is linked at the 2-position of the ring, thiazole, 1,2,4-thiadiazole, 1,2,3-triazole, pyrazole or pyridine ring.
6. Ring X is a thiazole ring.
7. A is a trimethylene, tetramethylene, pentamethylene, thiotrimethylene, thiotetramethylene, oxytrimethylene, oxytetramethylene, methylenethioethylene, methylenethiopropylene, methyleneoxyethylene or methyleneoxypropylene radical.
8. A is a methylenethioethylene radical.
9. $R^3$ is $NR^4R^5$ in which $R^4$ and $R^5$, which may be the same or different, are hydrogen atoms or alkyl, alkenyl or alkynyl radicals or $R^5$ is hydrogen and $R^4$ is a radical of the formula II.
10. $R^3$ is $NR^4R^5$ in which $R^5$ is a hydrogen atom and $R^4$ is a hydrogen atom or a methyl, ethyl, propyl, allyl or propargyl radical or a radical of the formula II in which m is 0 or 1, n is 2 or 3, E is an oxygen or sulphur atom and Het is a 2-guanidinothiazol-4-yl, 3-dimethylaminomethylphenyl or 2-dimethylaminomethylfur-5-yl radical.
11. $R^3$ is $NR^4R^5$ in which $R^5$ is a hydrogen atom and $R^4$ is a hydrogen atom or a methyl radical.

The preferred compound of the invention is 3-amino-4-[2-(2-[2,2,2-trifluoroethyl]guanidino)thiazol-4-ylmethylthio]ethylamino-1,2,5-thiadiazole 1-oxide and the pharmaceutically-acceptable acid-addition salts thereof.

A suitable pharmaceutically-acceptable acid-addition salt of the guanidine derivative of the formula I is, for example, a salt formed with hydrochloric, hydrobromic, phosphoric, sulphuric, acetic, citric or maleic acid.

The guanidine derivative of the invention may be manufactured by methods in which the actual chemical reactions involved are known in themselves. In the following processes, $R^1$, $R^2$, $R^3$, A, p and ring X have the meanings stated above, unless indicated otherwise. The following processes are provided as a further feature of the invention:

(a) for those compounds in which $R^3$ is a radical of the formula $NR^4R^5$, reaction of a compound of the formula VIII:

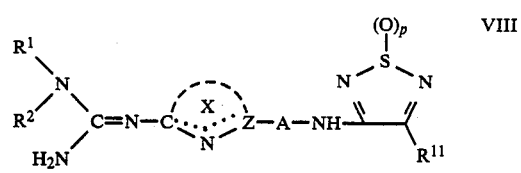

in which $R^{11}$ is a displaceable radical with a compound of the formula $HNR^4R^5$. $R^{11}$ may, for example, be a halogen atom, e.g., chlorine or bromine, or a phenoxy, phenylthio, 1–6C alkoxy, e.g., methoxy, or 1–6C alkylthio, e.g., methylthio, radical;

(b) for those compounds in which $R^3$ is a hydroxy radical, reaction of a compound of the formula VIII with hydroxide, i.e., potassium, lithium or sodium hydroxide;

(c) reaction of a compound of the formula IX:

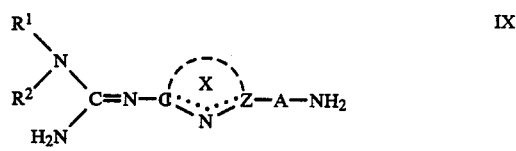

with a compound of the formula X:

in which $R^{11}$ is a displaceable radical. Examples of $R^{11}$ are given under process (a) above;

(d) construction of the guanidine radical attached to ring X by reaction of the appropriate thiourea, or a 1–6C S-alkyl or S-benzyl derivative thereof, or a salt of such a derivative, with the appropriate amine. The guanidine radical in the compound of the formula I contains three nitrogen atoms each of which carries different substituents. The appropriate amine for use in this reaction may therefore be ammonia, an amine of the formula $R^1R^2NH$ or an amine of the formula XI:

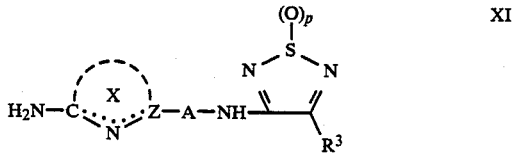

The reaction may be conducted using an excess of one of the reactants as a diluent or solvent, or an additional diluent or solvent, for example methanol or ethanol, may be used. In many cases it is advantageous to use a catalyst such as mercuric oxide, lead oxide or sodium hypochlorite. The reaction may be conducted at ambient temperature, or it may be accelerated or completed by the application of heat, for example by heating to the boiling point of the diluent or solvent;

(e) for those compounds in which the group inserted into A is an oxygen or sulphur atom or an NH or N-alkyl radical, reaction of a compound of the formula XII or XIII:

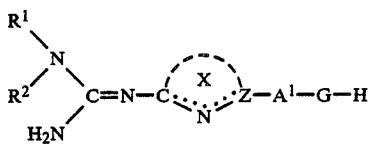

XII

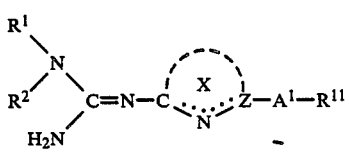

XIII with the compound of the formula XIV or XV, respectively:

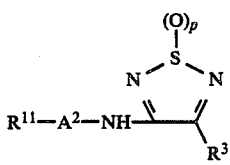

XIV

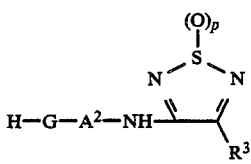

XV in which G is an oxygen or sulphur atom or an NH or N-alkyl radical, $R^{11}$ is a displaceable radical and $A^1$ and $A^2$ are fragments of A, including direct bonds, and are such that $A^1$—G—$A^2$ falls within the definition of A given above. $R^{11}$ is, for example a halogen atom, for example a chlorine, bromine or iodine atom. When $R^{11}$ is directly attached to ring X, $R^{11}$ is, for example, a methylsulphinyl or methylsulphonyl radical;

(f) for those compounds in which ring X is a thiazole ring, reaction of a compound of the formula XVI:

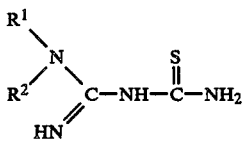

XVI with a compound of the formula XVII:

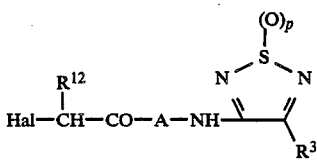

XVII in which Hal is a chlorine or bromine atom and $R^{12}$ is a hydrogen atom or the optional substituent on the thiazole ring. The reaction may be conducted in a diluent or solvent such as acetone and may be accelerated or completed by the application of heat, for example by heating to the boiling point of the diluent or solvent;

(g) construction of the guanidine radical attached to ring X by reaction of the appropriate cyanamide with the appropriate amine. Since the guanidine radical in the compound of the formula I contains only one unsubstituted nitrogen atom, there are two appropriate amines, namely the amine of the formula $R^1R^2NH$ or or of the formula XI given above;

(h) for those compounds in which Z is a nitrogen atom, reaction of a compound of the formula XVIII:

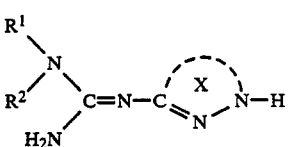

XVIII with a compound of the formula XIX:

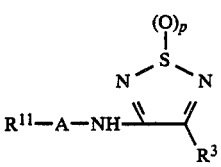

XIX in which $R^{11}$ is a displaceable radical. $R^{11}$ is, for example, a halogen atom, e.g., a chlorine or bromine atom.

When the process of the invention yields the compound of the formula I in the form of the free base, and an acid-addition salt is required, the compound of the formula I in the free base form is reacted with an acid which affords a pharmaceutically-acceptable anion.

The starting material of the formula VIII for use in process (a) or (b) may be prepared by reaction of a compound of the formula IX with a compound of the formula XX:

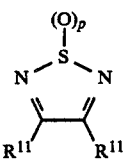

XX

The compound of the formula XX may itself be prepared by the methods described in UK published Patent Application No. 2067987.

The starting material of the formula IX for use in process (c) may be prepared by the methods described in European Patent Publication No. 30092. When $R^3$ is a hydroxy radical, the starting material of the formula X for use in process (c) may be prepared by reaction of the compound of the formula XX with a hydroxide, e.g., potassium, lithium or sodium hydroxide. When $R^3$ is of the formula $NR^4R^5$, the starting material of the formula X for use in process (c) may be prepared by reaction of a compound of the formula XX with a compound of the formula $R^4R^5NH$.

The compound of the formula XI for use in process (d) may be prepared by reaction of a compound of the formula XXI:

with a compound of the formula X.

The compounds of the formulae XII and XIII for use in process (e), of the formula XVI for use in process (f) and of the formula XVIII for use in process (h) may be prepared by the methods described in European Patent Publication No. 30092.

The compounds of the formulae XIV and XV for use in process (e), of the formula XVII for use in process (f) and of the formula XIX for use in process (h) may be prepared by suitable chemical modifications of the compound of the formula X.

The compound of the formula VIII for use in process (a) is a particularly valuable starting material for the manufacture of the compounds of the invention, and this compound is therefore provided as a further feature of the invention. Also part of the present invention are intermediates used in the preparation of the compounds of formula I, processes for preparing such compounds, methods for their use and pharmaceutical compositions containing them.

As noted above, the guanidine derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastrointestinal bleeding due to trauma.

The histamine H-2 antagonist activity may be demonstrated on standard tests, for example by the ability of the compound of the formula I to inhibit the histamine-induced uptake of aminopyrine into the acid space of parietal cells.

The aminopyrine test is carried out as follows:

Gastric mucosa from the New Zealand white rabbit is removed from the underlying muscle and washed in Buffer 1 which contains per liter: NaCl (8.007 g.), KCl (0.201 g.), Na$_2$HPO$_4$ (0.113 g.), KH$_2$PO$_4$ (0.204 g.), CaCl$_2$.2H$_2$O (0.132 g.) MgCl$_2$ (0.101 g.) and glucose (1 g.), adjusted to pH 7.4 with NaOH. The tissue is finely chopped, suspended in Buffer 1 and washed three times with Buffer 1. The tissue is then suspended in a dispersion medium of collagenase (Sigma Chemical Co., Type V; 100 mg.) and bovine serum albumin (Miles Laboratories Ltd., Fraction V; 100 mg.) in Buffer 1 (100 ml.) at 50 ml. per 10 g. net weight of tissue and incubated at 30° C. and pH 7.4 maintained by continuous monitoring, with stirring under an oxygen atmosphere. After 30 minutes the tissue is allowed to settle and the supernatant liquid is removed. Fresh dispersion medium (50 ml. per 10 g. wet weight of tissue) is added and incubation is continued with the tissue being largely dispersed into glands and whole cells after 40–60 minutes. Any remaining large pieces of tissue are removed by filtration through nylon mesh. The mixture of glands and cells is collected by centrifugation at 200× g and suspended in Buffer 1 containing 1% bovine serum albumin (Miles Laboratories Ltd., Fraction V). Finally the cells and glands are washed 3 times with Buffer 1 and suspended in Buffer 2 which contains Eagles MEM (500 ml.), Aprotinin (Sigma Chemical Co., 10 mg.) and HEPES (2-[4-(2-hydroxyethyl)piperazin-1-yl]ethanesulphonic acid; 150 mM., 20 ml.) adjusted to pH 7.4 with NaOH at 150 ml. per 10 g. net weight of tissue. The tissue suspension is stirred under an oxygen atmosphere at 32° C. for at least 1 hour before use. The tissue suspension is incubated with the test compound and aminopyrine (10 µM) labelled with $C^{14}$ on the dimethylamino group (0.1 µCi/ml.) for 20 minutes. The uptake of the aminopyrine is then stimulated by addition of histamine and the phosphodiesterase inhibitor ICI 63197 (*Biochem. Soc. Special Publication* 1, 1973, pp 127–132) to final concentrations of $10^{-5}$M. and $5\times10^{-7}$M. respectively. After 18 minutes the cells/glands are separated from the incubation medium by filtration of the suspension through glass microfibre filters. The cells/glands are quickly (less than 10 seconds) washed three times with ice-cold Buffer 1. The $C^{14}$ aminopyrine retained by the tissue is measured on a scintillation counter and the degree of inhibition of uptake by the test compound is calculated by reference to a control sample. The concentration of test compound giving 50% inhibition is then calculated graphically from a series of tests run at different concentrations.

A compound of Example 1 gave a 50% inhibition of uptake of aminopyrine below a concentration of 3 µM.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats or dogs provided with denervated fundic pouches, and whose gastric secretion is stimulated by administration of a secretagogue, for example histamine, pentagstrin, bethanechol or food.

The test in rats is carried out as follows:

Female rats (200–230 g.) are anesthetized by intramuscular administration of urethane (1.5 g/kg.) and the trachea cannulated. A soft tube is passed down the oesophagus into the stomach and secured by a tie in the neck region. A multi-orifice plastic tube (3 mm. diameter) is passed into the antral region of the stomach, via an incision in the duodenum, and tied in place by means of a ligature around the pylorus. Saline (9 g./l. NaCl) is perfused through the stomach via the oesophageal cannula at a rate of 7 ml./minute and collected into beakers from the pyloric outlet over periods of 10 minutes. Acid secretion is stimulated by subcutaneous administration of the specific H-2 agonist dimaprit in a loading dose of 10 mg./kg. followed by an infusion of 30 mg./kg./hour. Acid output is computed by titration of the 10 minute samples to an end point of pH 6.4 with 20 mM. NaOH. When secretion has reached a plateau (three consecutive readings within 5%) the test compound is administered intravenously via a cannula placed in the left external jugular vein. Secretion is then measured for a further 2 hours. A stock solution of each test compound is prepared (10 mg./ml. in DMSO) and appropriate dilution made with saline to enable injection in a dose volume of 1 ml./kg. (DMSO<2%).

The test in dogs provided with denervated fundic pouches is carried out as follows:

Male beagle dogs (14–22 kg.) are prepared with vagally denervated pouches of the fundic gland area by the method of Rudick et al. (*J. Surg. Res.* 1967, 7, 383). The animals are allowed 4–6 weeks to recover from surgery and a further period of 2–3 months prior to routine use, to allow for table training and standardization of secretory responses. The dogs are starved for 23 hours before use (water ad lib and during experiments they are lightly restrained in cloth slings. After rinsing the pouch with warm water, histamine is infused subcutaneously at a rate of 10 μg./minute. This dose of agonist produces a submaximal (60–90% of maximum) increase in acid output in all dogs used. Pouch secretions are collected over 15 minute periods into graduated glass test-tubes and the volume measured to the nearest 0.1 ml. A 500 μl sample is diluted with 5 ml. of saline and titrated to pH 7.0 with 100 mM.NaOH. Total acid output is computed from the product of acid concentration and volume of juice secreted. Compounds are administered intravenously (0.1 ml.kg.) via a cephalic vein or orally in a gelatin capsule when a secretory plateau (3 consecutive readings within 10%) has been attained. Secretion is measured for a period of 3 hours following administration of test compound.

The results obtained in the aminopyrine test are predictive of activity in the rat and dog tests.

According to a further feature of the invention there is provided a pharmaceutical composition which comprises a guanidine derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspension, emulsions, dispersible powders, suppositories, sterile injectable aqueous or oily solutions or suspensions, gels, creams, ointments or lotions.

In addition to the guanidine derivative of the formula I, the pharmaceutical composition of the invention for oral, rectal or parenteral administration may also contain, or be co-administered with, one or more known drugs selected from antacids, for example aluminium hydroxide-magnesium hydroxide mixtures; antipepsin compounds, for example pepstatin; other histamine H-2 antagonists, for example cimetidine or ranitidine; ulcer healing agents, for example carbenoxolone or bismuth salts; anti-inflammatory agents, for example ibuprofen, indomethacin, naproxen or aspirin; prostaglandins, for example 16,16-dimethylprostaglandin $E_2$; classical anti-histamines (histamine H-1 antagonists), for example mepyramine or diphenhydramine; anticholinergic agents, for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical anti-histamines (histamine H-1 antagonists), for example mepyramine or diphenhydramine and/or one or more steroidal anti-inflammatory agents, for example fluocinolone or triamcinolone.

A topical formulation may contain 1–10% w/w of the guanidine derivative of the invention. A preferred pharmaceutical composition of the invention is one suitable for oral administration in unit dosage form, for example a tablet or capsule which contains between 15 mg. and 500 mg. of the guanidine derivative, or one suitable for intravenous, subcutaneous or intramuscular injection, for example a sterile injectable containing between 0.1% and 10% w/w of the guanidine derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency and duration of action of the guanidine derivative of the present invention relative to cimetidine. Thus each patient will receive an oral dose of between 15 mg. and 1500 mg., and preferably between 20 mg. and 200 mg., of guanidine derivative or an intravenous, subcutaneous or intramuscular dose of between 1.5 mg. and 150 mg., and preferably between 5 mg. and 20 mg., of the guanidine derivative, the composition being administered 1 to 4 times per day. The rectal dose will be approximately the same as the oral dose. The composition may be administered less frequently when it contains an amount of guanidine derivative which is a multiple of the amount which is effective when given 1–4 times per day.

The invention is illustrated, but not limited, by the following Examples. The n.m.r. spectrum is quoted in δ relative to tetramethylsilane (δ=0) as internal standard (s=singlet, d=doublet, t=triplet, q=quartet). The temperatures are in degrees Centigrade.

EXAMPLE 1

A solution of 2-[2-(2,2,2-trifluoroethyl)guanidino]-4-[(2-aminoethyl)thiomethyl]thiazole (European Patent Publication No. 30092, Example 2; 2.1 g.) in methanol (20 ml.) was added dropwise to a stirred solution of 3,4-dimethoxy-1,2,5-thiadiazole 1-oxide (UK Patent Application No. 2067987, Example 4; 1.1 g.) in methanol (50 ml.) at 5°. The solution was stirred for 1.5 hours at 5°–10°. The intermediate 3-methoxy-4-[2-(2-[2,2,2-trifluoroethyl]-guanidino)thiazol-4-ylmethylthio]ethylamino-1,2,5-thiadiazole 1-oxide was not isolated, but anhydrous ammonia in methanol (6M, 20 ml.) was added. The solution was stirred for 17 hours at 25° and the solvent was evaporated. The residue was purified by chromatography on silica gel using dichloromethane/methanol 9:1 v/v as eluant. The purified product was obtained as an oil which was dissolved in acetone and the solution was treated with an excess of maleic acid in acetone. The salt which precipitated was recrystallized from ethyl acetate/ethanol to give 3-amino-4-[2-(2-[2,2,2-trifluoroethyl]guanidino)thiazol-4-ylmethylthio]ethylamino-1,2,5-thiadiazole 1-oxide maleate (2.0 g.), m.p. 113° (decomp.) having the following n.m.r. spectrum in $d_6$ dimethylsulphoxide: 2.8 (t, 2H); 3.55 (t, 2H); 3.7 (s, 2H); 4.15 (q, 2H); 6.2 (s, 2H); 6.8 (s, 1H).

EXAMPLE 2

A tablet containing 200 mg. of 3-amino-4-[2-(2[2,2,2-trifluoroethyl]guanidino)thiazol-4-ylmethylthio]ethylamino-1,2,5-thiadiazole 1-oxide may be prepared using ingredients in the following proportions:

|  | mg./tablet |
|---|---|
| Tablet Core | |
| Active agent | 200 |
| Lactose | 68.5 |
| Calcium carboxymethylcellulose | 22.5 |
| Polyvinylpyrrolidone | 6.0 |
| Magnesium stearate | 3.0 |
| Tablet Coat | |
| Hydroxypropylmethylcellulose | 4.5 |
| Polyethylene glycol | 0.9 |
| Titanium dioxide | 1.35 |

The active agent, lactose and calcium carboxymethylcellulose are mixed. An aqueous solution of polyvinylpyrrolidone is added, and the mass is then mixed until it is suitable for granulation. The mass is then granulated and dried. The magnesium stearate is blended with the dried granules and the resulting mixture is compressed into tablets. The tablets are film-coated using an aqueous or solvent suspension of hydroxypropylmethylcellulose, polyethylene glycol and titanium dioxide.

What is claimed is:

1. A guanidine derivative of the formula I:

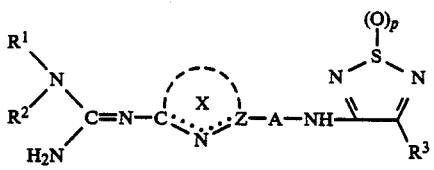

in which $R^1$ and $R^2$, which may be the same or different, are hydrogen atoms or branched or unbranched 1–10C alkyl, 3–8C cycloalkyl or 4–14C cycloalkylalkyl radicals, each alkyl, cycloalkyl or cycloalkylalkyl radical being optionally substituted by one or more halogen atoms selected from fluorine, chlorine and bromine atoms, provided that at least one of $R^1$ and $R^2$ is a halogen-substituted alkyl, halogen-substituted cycloalkyl or halogen-substituted cycloalkylalkyl radical, and provided that there is no halogen substituent on the carbon atom of the alkyl, cycloalkyl or cycloalkylalkyl radical which is directly attached to the nitrogen atom;

in ring X the dotted line is a double bond on one side of the nitrogen atom and Z is carbon or nitrogen atom such that ring X is 5-membered aromatic heterocyclic ring which contains at least one nitrogen atom and may optionally contain one or two additional hetero atoms selected from oxygen, nitrogen and sulphur atoms, and is selected from the group oxazole, thiazole, imidazole, 1,2,4-thiadiazole, 1,2,4-oxadiazole, 1,2,3-triazole, 1,2,4-triazole and pyrazole, which heterocyclic ring may, where possible, carry one or two optional substituents, the optional substituents on ring X being selected from fluorine, chlorine, bromine atoms and 1–6C alkyl, 1–6C alkoxy, 1–6C alkylthio, trifluoromethyl, hydroxy and amino radicals;

—A— is a 1–8C alkylene chain which is optionally substituted by one or two 1–3C alkyl radicals and into which is optionally inserted, as part of the backbone of the chain, one or two groups selected from oxygen and sulphur atoms and NH, 1–6C N-alkyl cis and trans vinylene, ethynylene, phenylene and 5–7C cycloalkyl radicals provided that no two insertions selected from oxygen and sulphur atoms and NH and N-alkyl radicals are directly attached one to the other and provided that when an insertion is directly attached to the NH radical it is other than oxygen or sulphur atom or an NH or N-alkyl radical, or —A— is a 5–7C cycloalkylene or phenylene radical;

P is 1 or 2;

$R^3$ is a hydroxy radical or a radical of the formula $NR^4R^5$ in which $R^4$ and $R^5$, which may be the same or different, are hydrogen atoms or radicals selected from 1–6C alkyl, 3–6C alkenyl, 3–6C alkynyl, 3–6C cycloalkyl, 4–10C cycloalkylalkyl, 2–6C hydroxyalkyl, 3–8C alkoxyalkyl, 3–8C alkylthioalkyl, 2–6C aminoalkyl, 3–8C alkylaminoalkyl, 4–12C dialkylaminoalkyl, amino, 1–6C alkylamino, 2–10C dialkylamino, 2,2,2-trifluoroethyl, 2-fluoro-ethyl, hydroxy, 1–6C alkoxy, 2,3-dihydroxypropyl, cyano, 2–6C cyanoalkyl, amidino, 2–6C alkylamidino, with the proviso that $R^4$ and $R^5$ cannot both be cycloalkyalkyl, amino, alkylamino, dialkylamino, hydroxy, alkoxy, cyano, amidino or alkylamidino radicals, and the pharmaceutically-acceptable acid-addition salts thereof.

2. A guanidine derivative as claimed in claim 1, in which $R^1$ and $R^2$ are selected from the group consisting of hydrogen atoms and 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3-tetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl, 2,2,3,3,4,4,4-heptafluorobutyl, 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl, 2-chloro-2,3,3,4,4-pentafluorocyclobutyl, (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl, (2-chloro-1,2,3,3,4,4-hexafluorocyclobutyl)methyl, methyl, ethyl, propyl, butyl, cyclopropyl, cyclobutyl, cyclopropylmethyl and cyclopropylbutyl radicals provided that at least one of $R^1$ and $R^2$ is a halogen-substituted radical;

in ring X the optional substitutes are selected from fluorine, chlorine and bromine atoms and methyl, methoxy, methylthio, trifluoromethyl, hydroxy and amino radicals;

—A— is trimethylene, tetramethylene, pentamethylene, thioethylene, thiotrimethylene, thiotetramethylene, thiopentamethylene, oxyethylene, oxytrimethylene, oxytetramethylene, methylenethiomethylene, methylenethioethylene, methylenethiopropylene, methyleneoxymethylene, methyleneoxyethylene, ethyleneoxyethylene, oxy-2-methylethylene, thiopropylenethiomethylene, oxyethyleneoxymethylene, iminopropylene, iminoethylene, vinylenepropylene, 1,3-phenylene, 1,3-cyclopentylene, methylene-1,4-phenylene, ethyleneoxymethylene-1,4-phenylene, oxy-1,3-phenylenemethylene or thiomethyleneethynylenemethylene radical;

P is 1;

$R^3$ is a hydroxy radical or a radical of the formula $NR^4R^5$ in which $R^4$ and $R^5$, which may be the same or different are hydrogen atoms or radicals selected from methyl, allyl, propargyl, cyclohexyl, cyclopropylmethyl, 2-hydroxyethyl, 2-methoxyethyl, 2-methylthioethyl, 2-aminoethyl, 2-methylaminoethyl, 2-dimethylaminoethyl, amino, methylamino, dimethylamino, 2,2,2-trifluoroethyl, 2-fluoroethyl, hydroxy, methoxy, 2,3-dihydroxypropyl, cyano, cyanomethyl, amidino, methylamidino, with the proviso that $R^4$ and $R^5$ cannot both be cyclopropylmethyl, amino, methylamino, dimethylamino, hydroxy, methoxy, cyano, amidino or methylamidino radicals;

and the pharmaceutically-acceptable acid-addition salts thereof.

3. The guanidine derivative as claimed in claim 2, in which ring X carries no optional substituent and is a thiazole, 1,2,4-thiadiazole, 1,2,3-triazole or pyrazole ring.

4. The guanidine derivative as claimed in claim 3, in which —A— is a trimethylene, tetramethylene, pentamethylene, thiotrimethylene, thiotetramethylene, oxytrimethylene, oxytetramethylene, methylenethioethylene, methylenethiopropylene, methyleneoxyethylene or methyleneoxypropylene radical.

5. The guanidine derivative as claimed in claim 4, in which $R^3$ is $NR^4R^5$ in which $R^5$ is a hydrogen atom and $R^4$ is a hydrogen atom or a methyl radical.

6. The guanidine derivative as claimed in claim 5, in which $R^2$ is a hydrogen atom and $R^1$ is a 2,2,2-trifluoroethyl radical.

7. A guanidine derivative selected from 3-amino-4-[2-(2-[2,2,2-trifluoroethyl]guanidino)thiazol-4-ylmethylthio]ethylamino-1,2,5-thiadiazole 1-oxide and the pharmaceutically-acceptable acid-addition salts thereof.

8. A compound of the following formula VIII:

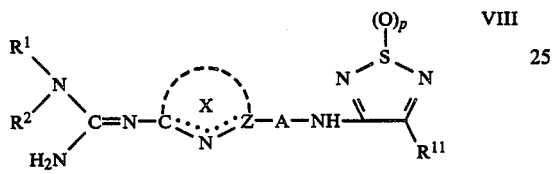

in which $R^1$ and $R^2$, which may be the same or different, are hydrogen atoms or branched or unbranched 1-10C alkyl, 3-8C cycloalkyl or 4-14C cycloalkylalkyl radicals, each alkyl, cycloalkyl or cycloalkylalkyl radical being optionally substituted by one or more halogen atoms selected from fluorine, chlorine and bromine atoms, provided that at least one of $R^1$ and $R^2$ is a halogen-substituted alkyl, halogen-substituted cycloalkyl or halogen-substituted cycloalkylalkyl radical, and provided that there is no halogen substituent on the carbon atom of the alkyl, cycloalkyl or cycloalkylalkyl radical which is directly attached to the nitrogen atom;

in ring X the dotted line is a double bond on one side of the nitrogen atom and Z is a carbon or nitrogen atom such that ring X is a 5-membered aromatic heterocyclic ring which contains at least one nitrogen atom and may optionally contain one or two additional hetero atoms selected from oxygen, nitrogen and sulphur atoms and is selected from the group oxazole, thiazole, imidazole, 1,2,4-thiadiazole, 1,2,4-oxadiazole, 1,2,3-triazole, 1,2,4-triazole and pyrazole, which heterocyclic ring may, where possible, carry one or two optional substituents, the optional substituents on ring X being selected from fluorine, chlorine and bromine atoms and 1-6C alkyl, 1-6C alkoxy, 1-6C alkylthio, trifluoromethyl, hydroxy and amino radicals;

—A— is a 1-8C alkylene chain which is optionally substituted by one or two 1-3C alkyl radicals and into which is optionally inserted, as part of the backbone of the chain, one or two groups selected from oxygen and sulphur atoms and NH, 1-6C N-alkyl cis and trans vinylene, ethynylene, phenylene and 5-7C cycloalkylene radicals provided that no two insertions selected from oxygen and sulphur atoms and NH and N-alkyl radicals are directly attached one to the other and provided that when an insertion is directly attached to the NH radical it is other than an oxygen or sulphur atom or an NH or N-alkyl radical, or —A— is a 5-7C cycloalkylene or phenylene radical;

P is 1 or 2; and $R^{11}$ is a displaceable radical.

9. A pharmaceutical composition which comprises a guanidine derivative as claimed in claim 1 in an amount effective to inhibit gastric acid secretion in a living animal and in association with a pharmaceutically-acceptable diluent or carrier.

10. A method of inhibiting gastric acid secretion in a living animal comprising administering to the animal, the pharmaceutical composition of claim 9.

* * * * *